(12) United States Patent
Schmidt et al.

(10) Patent No.: US 10,101,088 B2
(45) Date of Patent: Oct. 16, 2018

(54) SINTERING FURNACE FOR COMPONENTS CONSISTING OF A SINTERING MATERIAL, IN PARTICULAR FOR DENTAL COMPONENTS, AND A METHOD FOR SINTERING SUCH COMPONENTS

(71) Applicant: Sirona Dental Systems GmbH, Bensheim (DE)

(72) Inventors: Christian Schmidt, Bensheim (DE); David Figge, Bensheim (DE); Siegfried Gleditzsch, Heppenheim (DE); Peter Fornoff, Reichelsheim (DE)

(73) Assignee: Sirona Dental Systems GMBH, Bensheim (DE)

( * ) Notice: Subject to any disclaimer, the term of this patent is extended or adjusted under 35 U.S.C. 154(b) by 172 days.

(21) Appl. No.: 14/417,453

(22) PCT Filed: Jul. 24, 2013

(86) PCT No.: PCT/EP2013/065566
§ 371 (c)(1),
(2) Date: Jan. 26, 2015

(87) PCT Pub. No.: WO2014/016320
PCT Pub. Date: Jan. 30, 2014

(65) Prior Publication Data
US 2015/0247672 A1    Sep. 3, 2015

Related U.S. Application Data

(60) Provisional application No. 61/676,647, filed on Jul. 27, 2012.

(30) Foreign Application Priority Data

Jul. 27, 2012 (DE) .................. 10 2012 213 279

(51) Int. Cl.
  *F27B 17/02* (2006.01)
  *A61C 13/20* (2006.01)
  (Continued)

(52) U.S. Cl.
  CPC ............ *F27B 17/025* (2013.01); *A61C 13/20* (2013.01); *F27D 19/00* (2013.01); *F27D 21/00* (2013.01);
  (Continued)

(58) Field of Classification Search
  CPC .................................................. A61C 13/0004
  See application file for complete search history.

(56) References Cited

U.S. PATENT DOCUMENTS 4,498,865 A    2/1985   Schulmeyer
5,072,360 A    12/1991  Knorpp et al.
(Continued)

FOREIGN PATENT DOCUMENTS

DE    3231546 A1    3/1984
DE    3831539 A1    3/1990
(Continued)

OTHER PUBLICATIONS

German Office Action dated Jun. 25, 2013, issued in German Application No. 10 2012 213 279.1.
(Continued)

*Primary Examiner* — Gregory A Wilson
(74) *Attorney, Agent, or Firm* — Fitzpatrick, Cella, Harper & Scinto (57) ABSTRACT

The invention relates to a sintering furnace for components consisting of sintering material, especially dental components and in particular components consisting of ceramic, and a method for sintering such components. The sintering furnace 1 comprises a heatable furnace chamber 2 for the component 9 to be sintered, the furnace chamber 2 having a
(Continued)

wall section 6 to be opened for inserting the component 9 to be sintered into the furnace chamber 2. Drive means 10 are provided for mechanized opening and closing of the wall section 6, and a control 11 is provided for the drive means 10 that has an actuation element 12 for the drive means 10. Furthermore, a heating device 5 for the furnace chamber 2 is provided, and the control 11 causes the furnace chamber 2 to be heated. Actuating the control element 12 triggers the loading sequence of the control 11, and the drive means 10 are automatically actuated by the control 11 corresponding to the loading sequence. An additional subject is a method for operating the sintering furnace, as well as a computer program therefor.

39 Claims, 5 Drawing Sheets

(51) Int. Cl.
*F27D 19/00* (2006.01)
*F27D 21/00* (2006.01)

(52) U.S. Cl.
CPC .............. *F27D 2019/0003* (2013.01); *F27D 2019/0028* (2013.01); *F27D 2019/0081* (2013.01)

(56) References Cited

U.S. PATENT DOCUMENTS

| | | | |
|---|---|---|---|
| 5,656,564 A | 8/1997 | Nakayama et al. | |
| 6,558,821 B1 | 5/2003 | Shinosawa et al. | |
| 6,905,993 B2 | 6/2005 | Sakuta et al. | |
| 8,845,951 B2 | 9/2014 | Maginnis et al. | |
| 2010/0047731 A1 | 2/2010 | Zubler | |
| 2011/0006450 A1 | 1/2011 | Stephan et al. | |
| 2014/0339216 A1* | 11/2014 | Jussel | F27D 21/02 219/390 |
| 2015/0144611 A1* | 5/2015 | Miller | A61C 13/20 219/413 |

FOREIGN PATENT DOCUMENTS

| | | |
|---|---|---|
| DE | 4340200 A1 | 6/1995 |
| DE | 19824497 A1 | 12/1999 |
| DE | 102006032655 A1 | 1/2008 |
| EP | 2049857 A2 | 4/2009 |
| EP | 2101133 A1 | 9/2009 |
| EP | 2101547 A1 | 9/2009 |
| JP | 48-040638 Y | 11/1973 |
| JP | 05-172470 A | 7/1993 |
| JP | 2002-357391 A | 12/2002 |
| WO | 2009112324 A1 | 9/2009 |
| WO | 2012057829 A2 | 5/2012 |

OTHER PUBLICATIONS

International Preliminary Report on Patentability, PCT/EP2013/065566, dated Oct. 24, 2014.
International Search Report in International Application No. PCT/EP2013/065566 dated Dec. 10, 2013.
Office Action drafted May 26, 2017, in Japanese Patent Application No. 2015-523537.
Translation of Office Action in Japanese Patent Application No. 2015-523537, dated Jan. 23, 2018.

* cited by examiner

SINTERING FURNACE FOR COMPONENTS CONSISTING OF A SINTERING MATERIAL, IN PARTICULAR FOR DENTAL COMPONENTS, AND A METHOD FOR SINTERING SUCH COMPONENTS

TECHNICAL FIELD

The invention relates to a sintering furnace for components consisting of sintering material, especially dental components and in particular components consisting of ceramic, and a method for sintering such components. In comparison to technical components, components for dental restorations have a small volume, thin walls and small component cross-sections.

PRIOR ART

The material to be sintered is decisive for the design of a sintering furnace. In principle, metal or ceramic molded bodies are sintered that have been pressed from a powder and have been processed further in a milling or grinding process either directly or after an initial sintering process. The material determines the required temperature profile. The size and quantity of the components determine the size of the furnace as well as the temperature profile. The hotter the furnace, the thicker the wall of insulation. The size of the furnace and components and the desired heating rate determine the design of the heating system and the control behavior. The power supply also plays a role. The size of a dental furnace for a laboratory also differs from that of an industrial sintering furnace.

Today, thermal treatment processes, especially the complete sintering of dental restorations from presintered ceramics and metals using a sintering furnace, last between 80 minutes and several hours. The production process for a dental restoration requiring both preparatory steps as well as subsequent steps is greatly interrupted by this required time of an individual step. For example, so-called speed sintering of zirconium oxide requires at least 80 minutes. At present, the processing time can only be shortened if an alternative material is used that either requires a significantly shorter heat treatment or even no heat treatment at all.

A sintering furnace is known from the prior art comprising a heatable furnace chamber for the component to be sintered, the furnace chamber having a wall section that is opened to insert the component to be sintered into the furnace chamber. Drive means are provided for the mechanized opening and closing of the wall section, and a control is provided for the drive means that has an actuation element for the drive means. Furthermore, a heating device for the furnace chamber is provided, and the control causes the furnace chamber to be heated.

Such a sintering furnace was launched on the market in Germany in January of 2011 by Sirona Dental Systems GmbH of Bensheim, Germany. With this sintering furnace, the CAD/CAM process is significantly accelerated in the laboratory by reducing the sintering process of frameworks made of zirconium dioxide up to 75%. This time advantage was achieved by means of special heating elements, internal insulation, and sintering supports such as shells as well as prismatic or cylindrical molded bodies with plane-parallel base and loading surfaces.

With this sintering furnace, up to five-element bridge frameworks consisting of zirconium dioxide could be dense-sintered in 90 minutes. A multilayer bridge veneered with the assistance of a computer can therefore be produced within a single day. In addition, a selection can be made between regular and fast sintering programs depending on the type of material of the specific sintering ceramic. Regardless of the precisely indicated type of material, additional long- and short-duration sintering programs can be individually programmed. Furthermore, a time selection function is provided that allows the technician to perform sintering overnight. Shorter heating and cooling times ensure in principle that the device achieves significantly improved energy efficiency.

From WO 2012/057829 A2, it is known to place a dental prosthesis part in a guide in a reactor opened by a sealing flange such that the dental prosthesis part is placed in the center of a magnetic coil. By heating via induction or by igniting a microwave-induced plasma, the sintering time is reduced from hours to minutes. Zirconium oxide is the indicated coupling medium which is unsuitable for this purpose since the material only becomes electrically conductive in a useful manner starting at approximately 800° C.

Based on experiences from industrial production of ceramic powder metallurgical components, thermal treatment processes such as sintering are configured conservatively. It is, however, important for the heating of the components to always follow the temperature progression of the furnace in order to avoid temperature gradients since temperature gradients, depending on their configuration, lead to an uneven manifestation of the material properties and can be the cause of geometric distortions.

The object of the present invention is therefore to further reduce the production time while however achieving the material properties of the sintered component such that it still meets the requirements.

DESCRIPTION OF THE INVENTION

The sintering furnace according to the invention for components consisting of a sintering material, in particular for dental components and in particular for components consisting of ceramic, comprises a heatable furnace chamber for the component to be sintered, the furnace chamber having a wall section to be opened for inserting the component to be sintered into the furnace chamber, wherein a control is provided by means of which the heating of the furnace chamber can be controlled by a heating device for the furnace chamber. The control has means by which the time period of a loading sequence comprising the steps: opening, holding and closing the wall section while the furnace chamber is heated, can be detected individually or all together, and/or by which the temperature drop within the furnace chamber during said steps can be detected again individually or all together, and a plurality of set temperature profiles for the furnace chamber following the loading sequence is saved in the control, and one can be selected from a storage area by selection or comparison means provided in the control depending on the time period of one or all of the steps, and/or depending on the time period of the temperature drop in the furnace chamber again during one or all of the steps.

Possible means for detecting the time period of a loading sequence comprising the steps: opening, holding and closing the wall section while the furnace chamber is heated, individually or all together, are timers that are automatically triggered upon the movement of the wall section, or that detect when the wall section has left and/or reached an end position. The temperature drop in the furnace chamber during one or all of the steps can be detected by temperature gauges that are automatically read when the wall section moves, or that are read when the wall section has left and/or reached an end position. Instead of selecting a specific temperature profile, an appropriate temperature profile can be calculated from a plurality of available temperature profiles.

Advantageously, a control element can be provided which interacts with the control, wherein the actuation of the control element triggers the detection of the time period and/or the temperature drop by the control.

Furthermore, drive means can be provided for mechanized opening and closing of the wall section, wherein the drive means are actuated through the control with a control element corresponding to the loading sequence.

An additional sintering furnace according to the invention for components consisting of a sintering material, in particular for dental components and in particular for components consisting of ceramic, comprises a heatable furnace chamber for the component to be sintered, the furnace chamber having a wall section to be opened for inserting the components to be sintered into the furnace chamber. Drive means are provided for the mechanized opening and closing of the wall section, and a control is provided for the drive means that has an actuation element for the drive means. Furthermore, a heating device for the furnace chamber is provided, and the control causes the furnace chamber to be heated. To optimize the time period for performing the sintering process, the control has a preset, automated loading sequence for the drive means comprising the steps: opening, holding and closing the wall section, and to schedule heating of the furnace chamber. Actuating the control element triggers the control loading sequence, and the drive means are automatically actuated by the control corresponding to the loading sequence.

The cooling of the furnace chamber and associated temperature loss are largely known from the precisely-defined loading sequence such that the heating behavior of the component to be sintered, which is generally inserted at room temperature through the open, hot wall section into the furnace chamber, is also largely known.

Advantageously, the wall section to be opened can be designed as a seat for the component and, in an open state, forms a heated cooling zone that is placed at a distance from the furnace chamber. When the wall section is open, the component placed on the seat can be heated by the furnace chamber or possess a separate heating device. The control can have a cooling sequence for opening the wall section after the sintering process and for holding the wall section in the cooling zone, as well as for specifying the heating time of the furnace chamber or separate heating device, and there can be a control signal activated by the control which indicates that a cooling temperature has been reached in the cooling zone or the furnace chamber.

The use of a heated cooling zone under defined conditions in the cooling process enables a time-optimized, reproducible process and reduces the hazard of excessively fast cooling, as well as thermal shock, which prevents material damage.

To enable a short time period, the heating device can be designed as a resistance heater such that the furnace chamber has a heating rate of at least 1.0° C./s on average, and at most 6° C./s as a maximum after the loading sequence. The heating elements of the resistance heater can be operated from the beginning with maximum possible power consumption.

The control can advantageously have input means to select a temperature profile depending on a size of the component or geometric features such as a maximum wall thickness, or maximum component cross-section, or a volume of the component to be sintered, a material type of the component to be sintered, or a combination of several thereof.

The advantage of this is that an adaptation of the sintering process to the component to be sintered is possible by means of a time-optimized temperature profile.

Advantageously, the control can have an evaluation means for a bar code and/or other machine-readable ID with information on the component to be sintered, in order to automatically specify a temperature profile by considering a size of the component or geometric features such as a maximum wall thickness, or maximum component cross-section, or a volume of the component to be sintered, a material type of the component to be sintered, or a combination of several thereof.

The dimensions, volume, wall thicknesses and cross-sectional areas are known from the geometry of the component to be sintered. Temperature profiles can be assigned to the cited variables and combinations thereof, or temperature profiles can be generated by means of a process model to be determined empirically.

The invention furthermore relates to a method for sintering components consisting of a sintering material, in particular dental components and a sintering furnace, comprising the following steps:

a) opening a wall section of the furnace chamber with a preheated furnace chamber when the furnace heater is turned on;

b) loading the furnace chamber, in particular by bringing a component to be sintered that is placed on a seat outside the furnace chamber up to the open wall section;

c) closing the furnace chamber;

d) heating the furnace chamber up to a holding temperature over a time period HU2;

e) maintaining the holding temperature over a time period H;

f) opening the furnace chamber, either when the furnace heater is turned off or when the furnace heater is turned on;

g) for a first cooling stage, bringing the component with the seat into a heated, first cooling zone where it remains for a cooling period CD1;

h) for a second cooling stage, bringing the component with the seat out of the first cooling zone into a second cooling zone where it remains for a cooling period CD2;

i) removing the component from the seat, bringing the component into a third cooling zone for the third cooling stage by placing it on a base that is basically at room temperature, and waiting for a cooling period CD3.

j) wherein
  1. Steps a)-c) are performed for a maximum time period L of 2 minutes and preferably 1 minute;
  2. Step d) is performed for the maximum time period HU2 of 8 minutes, and preferably 4-5 minutes;
  3. Step e) is performed for the maximum time period H of 15 minutes, and preferably 4-8 minutes;
  4. Steps f) and g) are performed for the cooling time CD1 of at least 0.5 minutes, at most, however, 5 minutes;
  5. Step h) is performed for a cooling period CD2 of 1-5 minutes;
  6. Step i) is performed for a cooling time CD3 of at least 0.5 minutes, at most, however, 10 minutes.

With a sintering furnace operated according to one of such methods, production times of a maximum of 35 minutes can be achieved, and overall times of 15-20 minutes can be achieved within the indicated, preferable ranges. Such a shortening of the process time for heat treatment directly affects the reduction of the process throughput time by the amount of time saved. This enables the dental prosthesis part to be produced nearly free of interruption.

The heat treatment strongly depends on the component volume and design features such as wall thickness and component cross-section. It therefore may be advantageous if information is automatically evaluated and a temperature profile is automatically determined by an evaluation means for a bar code and/or an otherwise machine-readable ID with information on the size of the component or geometric features such as maximum wall thickness, or maximum component cross-section, or volume of the component to be sintered, material type of the component to be sintered, or a combination of several thereof of the component to be sintered.

In particular, the following are suitable as types of the component to be sintered for the dental region, and the list is not exclusive: Inlays, onlays, veneers, crown copings, full crowns, crown frameworks, bridges with a fully-anatomical design, and implant abutments.

Advantageously, the respective time periods of steps a) to i) can be automatically determined by the evaluation means from information on the components be sintered, in particular the time period H from step e), wherein the maximum wall thickness of the component to be sintered, the volume of the component to be sintered, the material type or the type of the component to be sintered, or a combination of several thereof can be automatically evaluated.

A controlled, first cooling zone can be provided if the heated cooling zone of the first cooling stage is heated by the sintering furnace, in particular by the furnace chamber.

The method can be advantageously used for components consisting of sinterable oxide ceramics or glass ceramics, as well as sinterable non-precious metallic materials produced by powder metallurgy, in particular based on CoCr, CoCrMo, CoCrW or CoCrMoW.

In addition, it is advantageous to sinter dental components consisting of zirconium oxide and translucent zirconium oxide with wall thicknesses of 0.1 to 6 mm using the method.

The wall thickness of crown copings can advantageously be 0.3 to a maximum of 0.8 mm, and the material thickness of full crowns can be 0.3 to a maximum of 4 mm, and the connector cross-section of the bridge structures can be a maximum of 28 $mm^2$.

Advantageously, the temperature in the furnace chamber during step e) can be at least large enough to enable sintering with a degree of sintering of at least 80% at this temperature and the preset time period, and the temperature in the furnace chamber during step e) can be at most enough to prevent a disadvantageous phase transition above the temperature.

The sintering must possess a degree of sintering at which the material properties required by the standard and the optical properties within the components are achieved. The degree of sintering is described by the relative density, and a relative density>99.5% is not absolutely necessary in order to achieve the necessary properties.

Advantageously, the temperature in the furnace chamber during step e) for a dental zirconium oxide of the basic zirconium oxide type $ZrO_2$ with an added portion of 4.5-6% by weight of yttrium oxide $Y_2O_3$ can be at least 1,550° C. and at most 1,600° C. This prevents a disadvantageous phase transition for the holding time.

Advantageously, the furnace chamber can have an average heating rate of at least 1.0° C./s and at most 6° C./s as the maximum value during step d).

This allows distortion during heating of the component to be sintered to be controlled to an appropriate degree in practice, and the heat can be provided with for example a household power of, for example, 230 V and a maximum 16 amp fuse, wherein 15 amps are also sufficient if the local power supply requires such a limitation.

A further subject of the invention is a computer program stored on a machine-readable carrier with a machine-readable code for executing a method to control temperature during a sintering process using a sintering furnace, wherein the temperature profile is selected for the sintering process for the component to be sintered depending on the loading sequence of the sintering furnace for the component to be sintered.

BRIEF DESCRIPTION OF THE DRAWINGS

The invention will be explained with reference to the drawing. In the figures.

EMBODIMENT EXAMPLE

Figure 1:
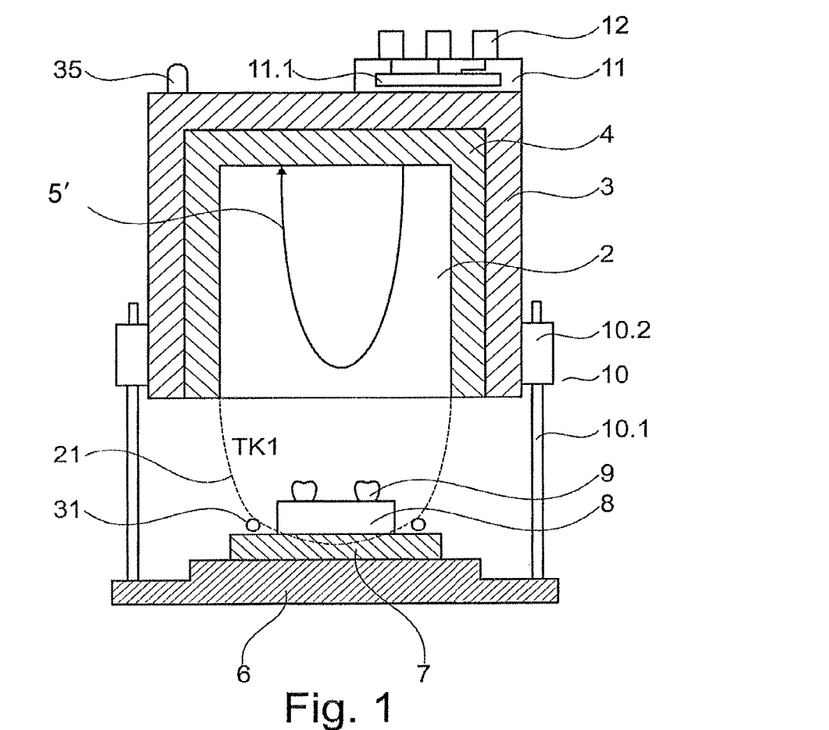
FIG. 1 shows a part of a sintering furnace according to the invention for components consisting of a sintering material, in particular for dental components.

FIG. 1 shows a part of a sintering furnace 1 (FIG. 2) that has a furnace chamber 2 with walls provided with insulation 4 to shield the hot furnace chamber against the surroundings. A heating device 5 with heating elements is situated in the furnace chamber 2 to heat the furnace chamber 2. Flow 5' is caused by heating device 5. The furnace chamber has a wall section 6 to be opened for inserting the component to be sintered into the furnace chamber which, in this case, is the bottom wall section, i.e. the floor of the furnace chamber 2. The floor 6 also has insulation 7 on which a base 8, also termed a support 8, is placed for the components 9 to be sintered. Brackets, or vertical pins consisting of ceramic, or high-melting-point metal are also possible as the support 8 on which the dental component is placed. A separate heating device can also be provided over a heating element 31.

Drive means 10 are provided for the mechanized opening and closing of the wall section 6, whereby the wall section 6 can be lowered to open the furnace chamber 2 and lifted to close the furnace chamber 2.

For the heating device 5 and drive means 10, a control 11 is provided that also comprises control elements 12 for the drive means 10 consisting of a spindle rod 10.1 and a driven spindle nut 10.2, and possibly for entering additional parameters to influence the heating device 5. Separate controls and different lifting devices can also be provided.

The control 11 is designed so that it triggers a preset, automated loading sequence for the drive means 10.1, 10.2 comprising the steps: opening, holding and closing the wall section 6, and to schedule heating 5 of the furnace chamber 2, and actuation of the control element 12 triggers the loading sequence of the control of 11, and the drive means 10 are automatically actuated by the control corresponding to the loading sequence. Furthermore, an evaluation means 11.1 is included for a CAD data record.

Instead of automating the execution of the loading sequence, it can also be performed exclusively manually, or be triggered manually, wherein the sequence of the individual steps of the loading sequence is rendered perceptible to the user by a signal indicator 35, e.g. visual or acoustical. The signal indicator 35 is also connected to the control 11.

An additional embodiment records the time period of the individual steps of the loading sequence and/or the temperature drop of the loading sequence which can then proceed largely as desired, and the temperature profile of the furnace chamber is correspondingly adapted to the subsequent sintering process, or the temperature profile is selected from several profiles.

When the furnace chamber 2 is in the described open state after the sintering process, the support 8 on which the sintered component 9 is located is held at a distance from the furnace chamber 2 and is located in a first cooling zone 21 heated by the furnace chamber 2 to temperature TK 1.

Figure 2:
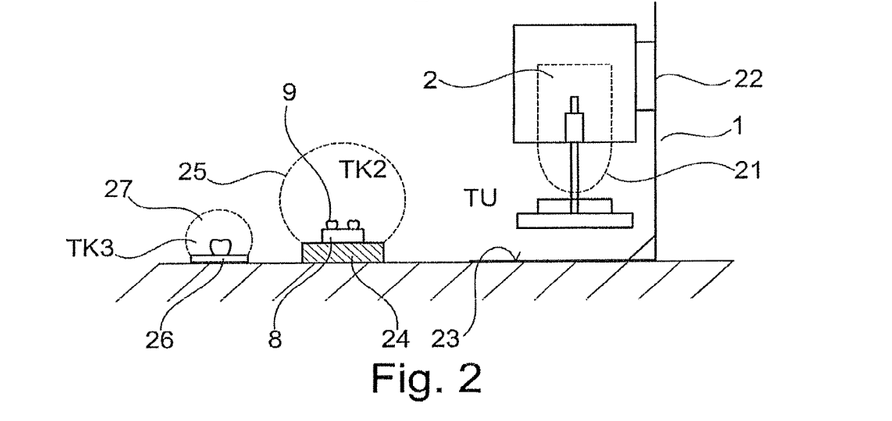
FIG. 2 shows the part from FIG. 1 in a side view of the entire sintering furnace.

FIG. 2 shows a side view of the entire sintering furnace 1, wherein the part from FIG. 1 is fastened to the rear wall 22 that sits on a foot part 23.

The sintering furnace 1 generally stands on a work table or a working plate (not shown) and, despite its weight, can still be lifted and moved when necessary e.g. for cleaning reasons.

In the depicted, open state of the furnace chamber, the seat on which the sintered component is located is removed from the first heated cooling zone 21 at temperature TK1. On the sintering furnace 1 or directly proximate thereto, a second cooling stage is provided which involves no heating and has a heat-resistant base 24 at room temperature to receive the support 8 with the component 9 placed thereupon. In contrast to the ambient temperature, the still-heated seat 8 offers a cooling zone 25 with a temperature distribution at temperature TK2 which is greater than the ambient temperature TU.

A third cooling stage comprises a base 26 with high heat removal such as a metallic plate at room temperature, so that the component placed thereupon is exposed to the ambient temperature, and a third cooling zone exists at temperature TK3.

As the furnace temperature increases, the heating rate decreases degressively. The heating rate directly after the loading sequence is 3.3-3.5° C./min during the first minute. As of the second minute, it is 1.0-1.25° C./s. During the final minute, the heating rate drops to 0.1-0.12° C./rain. On average, the heating rate after the loading sequence lies between 1.16 and 1.25° C./min.

Figure 3:
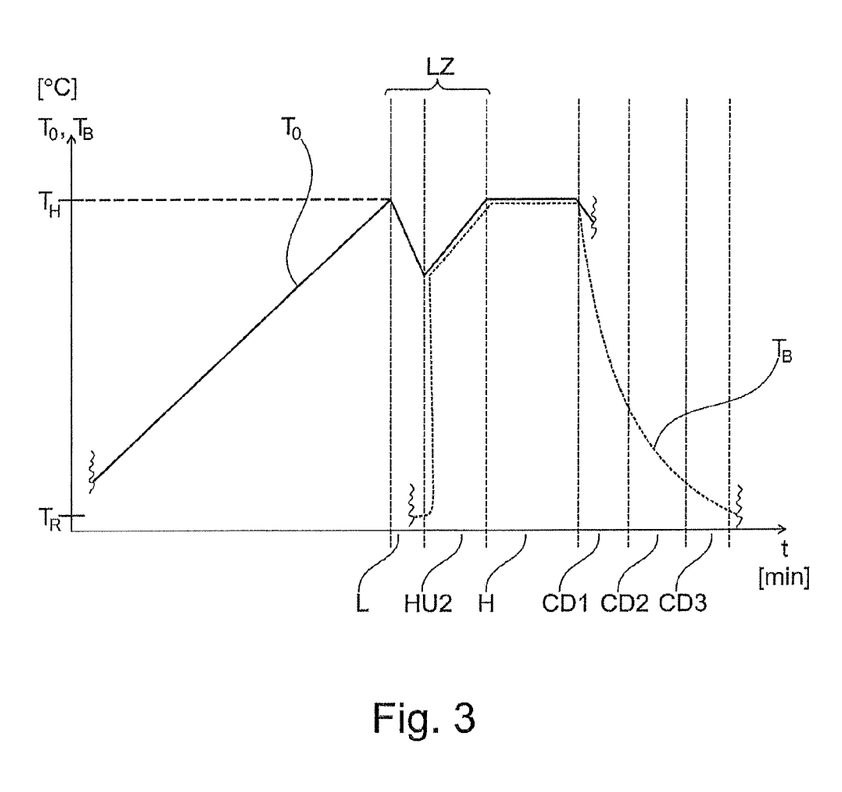
FIG. 3 shows a temperature profile for the method according to the invention for sintering such components.

FIG. 3 shows a temperature profile for the method according to the invention for sintering such components in a sintering furnace for the furnace temperature "$T_o$" and component temperature "$T_B$".

The effective processing time is shortened by eliminating the heating time, a shorter holding time, and controlled cooling using three cooling zones that each have specific temperature distributions. The furnace can be preheated simultaneous with upstream processes so that the relevant overall processing time is only the time from loading the furnace until grasping the parts after cooling. This time can be less than 15 minutes depending on the durability and type of material. In conjunction with such a dental CAD/CAM system, the shortened processing throughput time makes treatment known as chairside treatment possible for the dentist. This means that the patient can be supplied in just one visit with a fixed dental prosthesis due to the fast production of a restoration.

The dental technician can thereby produce restorations without a significant interruption. Individual orders can be produced without interruption after the order is received. The shorter throughput time makes a quicker response time possible for the dental technician for rush orders.

Before actual sintering, the furnace is preheated to a holding temperature $T_H$ of, for example, 1600° C. for zirconium oxide. The component to be sintered can be produced in a simultaneous production process.

The furnace chamber 2 is opened in a heated state for loading, and the component base 8 and components 9 are at room temperature Tu during loading.

Since no material is arbitrarily resistant to thermal shock, the fast heating and short holding time are followed by a controlled and specific cooling process that is configured in a time-optimized manner while retaining the necessary material properties.

The method following the preheating of the furnace chamber 2 up to at least the holding temperature $T_H$ desired for sintering is started by actuating the control element 12 that triggers the loading sequence contained within the control 11. It does not matter how long the furnace chamber was held at the holding temperature $T_H$ before the actuating element 12 was actuated.

The following steps are then run automatically as a loading sequence comprising opening, holding and closing for a time period L of a maximum of 2 minutes, and preferably 1 minute:

a) opening a wall section 6 of the furnace chamber 2 with a preheated furnace chamber 2 when the furnace heater is turned on;

b) loading the furnace chamber, in particular by bringing a component 9 to be sintered that is placed on a seat 8 outside of the furnace chamber 2 up to the open wall section 6;

c) closing the furnace chamber 2.

By being placed on the wall section 6 when the component 9 to be sintered is inserted into the furnace chamber placed on the seat 8, and given the known loading sequence, the component 9 is heated with a known temperature profile since the loading sequence is known.

It is also possible to preheat the furnace chamber 2 to a higher holding temperature $T_H'$ to keep the temperature drop within the furnace chamber during the time period required for loading the furnace chamber, and the associated opening of the furnace chamber, as slightly below the desired holding temperature $T_H$ for sintering as possible, and to reduce the heating time after opening.

After the loading cycle, which results in a specific cooling of the furnace chamber 2 due to the known time characteristics, the furnace chamber 2 is heated up to a desired holding temperature $T_H$ for sintering during a time period HU2 of a maximum of 8 minutes and preferably 4-5 minutes, wherein the component 9 is correspondingly also heated during this time.

To perform sintering at a constant holding temperature $T_H$, the holding temperature $T_H$ is maintained during a time period H of a maximum of 15 minutes, and preferably 4-8 minutes.

After said sintering at a constant holding temperature $T_H$, the furnace chamber 2 is opened, either when the oven heating 5 is turned off, or when the oven heating 5 is turned on, and the component 9 with the seat 8 are brought into a heated, first cooling zone 21 for a first cooling stage, and remain for a cooling time period CD1 of at least 0.5 minutes, but a maximum of 5 minutes.

In a second cooling stage, the component with the seat is moved from the first cooling zone 21 into a second cooling zone 25 and remains for a cooling time period CD2 of 1-5 minutes. The seat 8 itself radiates heat.

Finally, the component 9 is removed from the seat 8, and the component is moved to a third cooling zone 27 for the third cooling stage by being placed upon a base 26, essentially at room temperature Tu, and remains for a cooling time period CD3 of at least 0.5 minutes and a maximum, however, of 10 minutes. The heat in this instance only originates from the component 9 itself.

The temperature TK1, TK2, TK3 in the sequential cooling zones gradually decreases; the first cooling zone is hotter than the second which in turn is hotter than the third. If necessary, the second and third cooling zones can also be heated.

Figure 4:
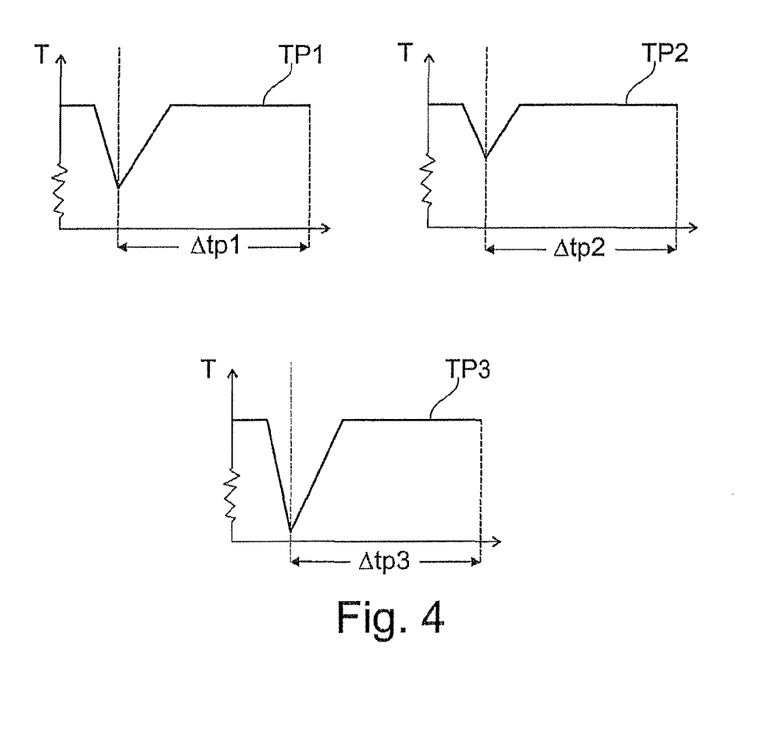
FIG. 4 shows different temperature profiles depending on the temperature drop and/or the time period of the loading sequence.

FIG. 4 shows the different temperature profiles TP1, TP2 and TP3 depending on the temperature drop and/or the time period of the loading sequence, wherein different time periods delta-tp1, delta-tp2 and delta-tp3 result. The shorter the loading sequence and the shorter the temperature drop, the shorter the heating and holding phase following the loading sequence.

Figure 5:
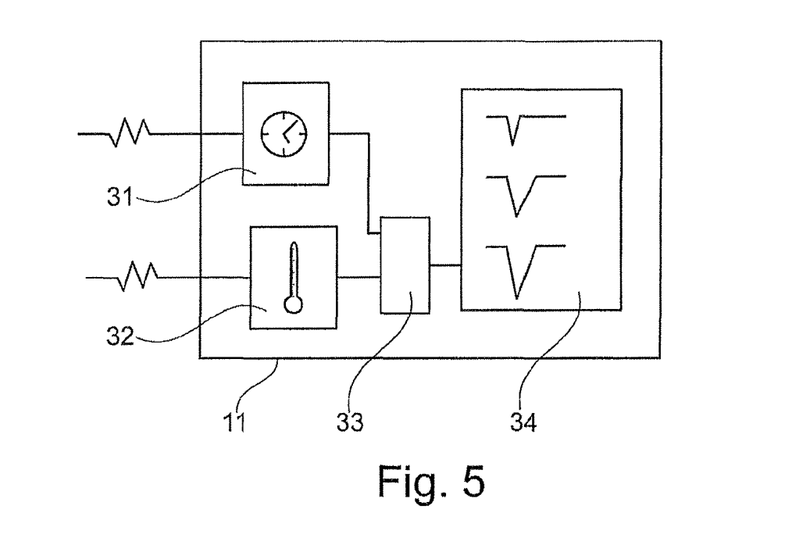
FIG. 5 shows a schematic of the control.

FIG. 5 shows a schematic of a part of the control 11 in which means 31 for detecting the time period of the loading sequence and means 32 for detecting the temperature interact with selective or comparative means 33 in order to select the appropriate temperature profiles for the furnace chamber from a plurality of temperature profiles archived in a memory area 34, and then operate the furnace chamber according to the selected temperature profile.

For zirconium oxide and translucent zirconium oxide, the following dimensions of the design features for shortening the process time are assumed in FIGS. 4A-C:
- with crown copings according to FIG. 4A, the wall thickness indicated by the two arrows lies within a range of 0.3 to a maximum of 0.8 mm;
- with full crowns according to FIG. 4B, the material thickness indicated by the two arrows lies within a range of 0.3 to a maximum of 4 mm;
- with bridge structures according to FIG. 4C, the connector cross-section indicated by the two right arrows is a maximum of 20 mm$^2$, which corresponds to a thickness of 5 mm, wherein the cross-section of a pontic indicated by the two left arrows can also be larger since the degree of sintering achieved in the sintering process remains sufficient at that location to ensure the required strength.

Figure 6A:
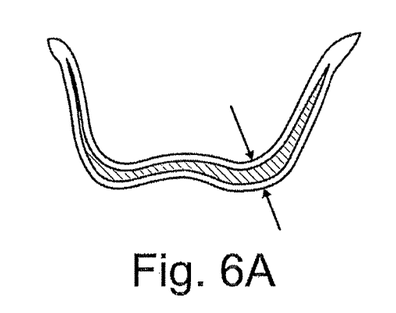
FIGS. 6A-C show typical dental components.
Figure 6B:
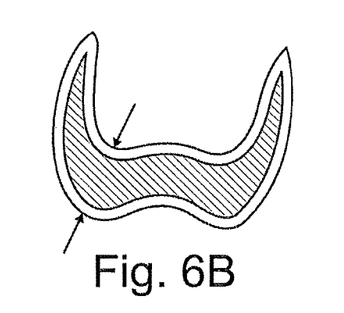
Figure 6C:
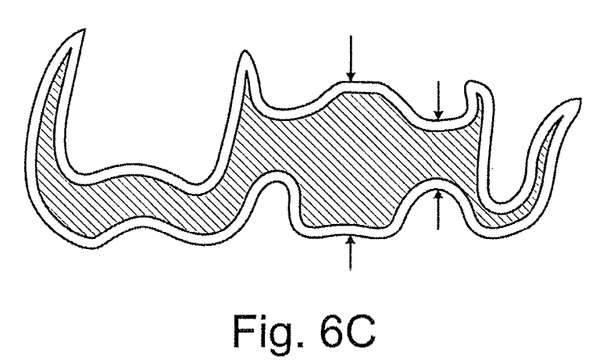
Figure 7:
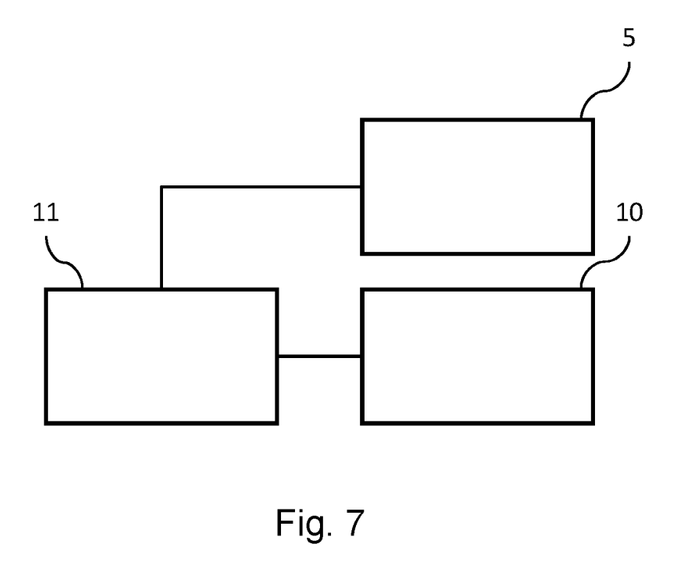
FIG. 7 shows a block diagram of the control, heating device, and drive means.

Given these geometric dimensions depicted in FIGS. 6A-C, dental restorations are heated faster with comparable material and energy use. Depending on the design features of the wall thickness and cross-section, the parameters of heat treatment such as the heating and cooling rates and holding times can be predetermined with the support of software.

A plurality of temperature stages with specific temperature fields was identified experimentally for zirconium oxide:

After expiration of the holding time, the furnace chamber is opened, the seat 8 together with the component 9 are removed from the furnace chamber 2, but remain on the wall section 6 of the furnace chamber 2. The temperature radiation field of the furnace chamber 2 and the temperature radiation field of the wall section 6, the seat 8 and the component 9 overlap, and have a buffering effect on the temperature equilibrium with the colder room air at temperature $T_u$ which is significantly cooler. Once a seat temperature of <600° C. and >275° C. is reached, there is a transition to cooling stage 2.

To communicate to the user the transition to cooling stage 2, the furnace control can emit an acoustic signal that is triggered when 1000° C. is measured at a temperature measuring site in the furnace chamber. It has been proven that this is sufficient since this temperature in the furnace chamber corresponds to a surface temperature of the opened wall section 6 or the seat 8 in the indicated area. The notification signal can also be visual, for example from an indicator light that may flash, or from a notification on the display which can also flash.

The seat 8 together with the component 9 is removed from the first cooling zone 21 and hence from the temperature radiation field of the furnace chamber 2 that are placed on a heat-resistant base at room temperature. Heat is now exchanged between room temperature $T_u$ and the seat 8 together with the component 9 and forms the second cooling zone 25.

The seat now assumes the function of the temperature buffer to compensate for possible thermal shock.

After 2 minutes, the temperature of the seat 8 lies between 100° C. and 200° C. depending on the loading. The component 9 can now be transferred to the third cooling stage.

In the transition from cooling stage 2 to cooling stage 3, the component 5 is placed from the seat 8 onto a metal base 26 at room temperature $T_u$ until, after a maximum of 2 minutes, it is warm to the touch, and can be processed further.

The fixed temperature ranges during cooling can be maintained by actively or passively supported heated bases.

The process is suitable in principle for crowns, crown copings, full crowns, bridges, bridge frameworks, inlays and veneers. The aforementioned parameters were determined for sintering zirconium oxide and translucent zirconium oxide.

If the holding temperature, holding time and cooling stages are adapted, the described process can also be used for other sinterable oxide ceramics or glass ceramics. This also holds true for sinterable NEM materials based on CoCr, CoCrMo, CoCrW or CoCrMoW produced by powder metallurgy.

A temperature profile for the sintering procedure is selected with the computer program, depending on the loading sequence of the sintering furnace.

The invention claimed is:

1. A sintering furnace for dental components, comprising:
a furnace chamber that includes a movable wall section configured to move between an opened position and a closed position, the wall section includes a seat for a component to be sintered;
a heating device configured to heat the furnace chamber;
a controller configured to control the heating device so as to control a temperature in the furnace chamber; and
a memory storing a plurality of temperature profiles for a sintering process,
wherein the controller is constructed to:
  (i) execute a loading sequence, while the furnace chamber is heated by the heating device, that includes steps of:
    opening the wall section of the furnace chamber for a first time, holding the wall section of the furnace chamber in the opened position while a component to be sintered is loaded on the seat, and closing the wall section of the furnace chamber, (ii) measure time periods for one or more of the opening, holding, and closing steps of the loading sequence, (iii) detect one or more temperature drops within the furnace chamber during one or more of the opening, holding, and closing steps of the loading sequence, (iv) select a temperature profile for the sintering process from the plurality of temperature profiles based on one or more of the measured time periods and/or one or more of the detected temperature drops within the furnace chamber, (iv) execute the sintering process of:

heating the furnace chamber, after the loading sequence is completed, to a holding temperature over a first time period based on selected temperature profile, and maintaining the holding temperature over a second time period, and (v) execute a cooling process of:

opening the wall section of the furnace chamber for a second time to bring the seat of the wall section into a heated first cooling zone for a first cooling period, and causing a signal indicating an expiration of the first cooling period and a transition to a second cooling period corresponding to a second cooling zone to be emitted, wherein a temperature in the second cooling zone is lower than a temperature in the first cooling zone.

2. The sintering furnace according to claim 1, further comprising:

a control element, wherein actuation of the control element causes the controller to execute the loading sequence, measure the time periods, and detect the one or more temperature drops.

3. The sintering furnace according to claim 1, further comprising:

a drive unit constructed to move the wall section between the opened position and the closed position, wherein the drive unit is controlled by the controller according to the loading sequence in response to actuation of a control element.

4. The sintering furnace according to claim 1, wherein the heating device is controlled to heat the furnace chamber at an average heating rate of at least 1.0° C./s.

5. The sintering furnace according to claim 1, wherein the controller is further configured to select the temperature profile from the plurality of temperature profiles stored in the memory based on at least one of: (i) a size of a component to be sintered, (ii) one or more geometric features of the component to be sintered, including: a maximum wall thickness, a maximum component cross-section, and a volume of the component to be sintered, and (iii) a material type of the component to be sintered.

6. The sintering furnace according to claim 1, further comprising:

an evaluation unit configured to acquire information on a component to be sintered, wherein the controller is further configured to select the temperature profile based on the acquired information.

7. The sintering furnace according to claim 1, wherein the heating device is controlled to heat the furnace chamber at a maximum heating rate of 6° C./s.

8. A sintering furnace for dental components, comprising:

a furnace chamber that includes a movable wall section configured to move between an opened position and a closed position, the wall section includes a seat for the component to be sintered;

a heating device configured to heat the furnace chamber;

a memory storing:

(i) a preset loading sequence that includes steps of:

opening the wall section of the furnace chamber for a first time, holding the wall section of the furnace chamber in the opened position while a component to be sintered is loaded on the seat, and closing the wall section of the furnace chamber, wherein the furnace chamber is heated by the heating device during the preset loading sequence, and (ii) a temperature profile for a sintering process; and a controller constructed to:

(i) control a temperature in the furnace chamber, (ii) execute the preset loading sequence, (iii) control the heating device during the sintering process in accordance with the temperature profile following the preset loading sequence, wherein the sintering process includes steps of:

heating the furnace chamber, after the loading sequence is completed, to a holding temperature over a first time period based on the temperature profile, and maintaining the holding temperature over a second time period, and (iv) perform a cooling sequence of:

opening the wall section of the furnace chamber for a second time to bring a seat of the wall section into a heated first cooling zone for a first cooling period, and causing a signal indicating an expiration of the first cooling period and a transition to a second cooling period corresponding to a second cooling zone to be emitted, wherein a temperature in the second cooling zone is lower than a temperature in the first cooling zone.

9. The sintering furnace according to claim 8, further comprising:

a drive unit constructed to move the wall section between the opened position and the closed position, wherein the controller is further configured to control the drive unit according to the preset loading sequence in response to actuation of a control element.

10. The sintering furnace according to claim 8, wherein the controller is further configured to control the drive unit to open the wall section such that the seat is located a predetermined distance from the furnace chamber.

11. The sintering furnace according to claim 10, further comprising:

another heating device, wherein the controller is further configured to operate the heating device or the other heating device to heat the seat of the wall section while the seat of the wall section is held in the first cooling zone.

12. The sintering furnace according to claim 11, further comprising:

at least one temperature sensor configured to measure a temperature in at least one of the first cooling zone or the furnace chamber, wherein the controller is further configured to issue a control signal when the at least one temperature sensor indicates that a cooling temperature has been reached.

13. The sintering furnace according to claim 8, further comprising:

at least one signal indicator constructed to indicate which of the opening, holding, and closing steps is currently being performed.

14. A method for sintering a dental component, comprising:

opening a wall section of a furnace chamber for a first time;

loading the furnace chamber by placing a component to be sintered on a seat of the wall section while the wall section is opened;

closing the wall section of the furnace chamber;

heating the furnace chamber to a holding temperature over a first time period;

maintaining the holding temperature over a second time period;

opening the wall section of the furnace chamber for a second time to bring the seat of the wall section into a heated first cooling zone for a first cooling period;

moving the component to a second cooling zone for a second cooling period, wherein a temperature in the second cooling zone is lower than a temperature in the first cooling zone.

15. The method according to claim 14, further comprising: moving the component to another cooling zone, prior to moving the component to the second cooling zone, for another cooling period between one and five minutes, inclusive.

16. The method according to claim 15, wherein the other cooling period is between one and five minutes, inclusive.

17. The method according to claim 14, further comprising:

acquiring information on the component to be sintered; and automatically determine a temperature profile for the sintering method based on the acquired information.

18. The method according to claim 17, wherein the time periods for the heating and maintaining steps and the cooling periods for the opening and moving steps are automatically determined based on the information on the component to be sintered.

19. The method according to claim 17, wherein the information on the component to be sintered includes at least one of: a duration of the second cooling period, a maximum wall thickness of the component to be sintered, a volume of the component to be sintered, a type of the component to be sintered, and a component material type.

20. The method according to claim 14, wherein the heated cooling zone is heated by a heater within the furnace chamber.

21. The method according to claim 14, wherein the component to be sintered is comprised of one or more of: sinterable oxide ceramics, glass ceramics, or sinterable non-precious metallic materials.

22. The method according to claim 14, wherein the component to be sintered is comprised of zirconium oxide and translucent zirconium oxide and has a wall thickness of 0.1 mm to 6 mm.

23. The method according to claim 14, wherein the component to be sintered includes a crown coping with a wall thickness of 0.3 mm to 0.8 mm, inclusive.

24. The method according to claim 14, wherein the holding temperature in the furnace chamber during the second time period is high enough to allow a degree of sintering to be at least 80%.

25. The method according to claim 14, wherein the holding temperature in the furnace chamber during the second time period is between 1,550° C. and 1,600° C., inclusive.

26. The method according to claim 14, wherein an average heating rate of the furnace chamber is between 1.0° C./s and 6° C./s.

27. The method according to claim 14, wherein the steps of (i) opening the wall section of the furnace chamber for the first time, (ii) loading the furnace chamber, and (iii) closing the wall section of the furnace chamber, are performed within a time period ranging from two seconds to eight minutes, inclusive.

28. The method according to claim 27, wherein the time period is one minute.

29. The method according to claim 14, wherein a maximum time for the first time period is eight minutes.

30. The method according to claim 14, wherein the first time period is between four and five minutes, inclusive.

31. The method according to claim 14, wherein a maximum time for the second time period is eight minutes.

32. The method according to claim 14, wherein the second time period is between four and eight minutes, inclusive.

33. The method according to claim 14, wherein a total time for opening the wall section of the furnace chamber for the second time and for the first cooling period is between 30 seconds and five minutes, inclusive.

34. The method according to claim 14, wherein the second cooling period is between 30 seconds and 10 minutes, inclusive.

35. The method according to claim 14, wherein the component to be sintered includes a full crown with a material thickness of 0.3 mm to 4 mm.

36. The method according to claim 14, wherein the component to be sintered includes a bridge structure, and a connector cross-section of the bridge structure is a maximum of 28 mm$^2$.

37. The method according to claim 14, wherein the holding temperature in the furnace chamber during the second time period is below a temperature where a phase transition of the component to be sintered occurs.

38. The method according to claim 14, wherein the furnace chamber is preheated when the wall section is opened for the first time.

39. A non-transitory computer readable medium storing a set of computer readable instructions which when executed by a controller for a sintering furnace cause the controller to perform steps of:

opening a wall section of a furnace chamber for a first time to an opened position;

holding the wall section of the furnace chamber at the opened position while a component to be sintered is placed on a seat of the wall section;

closing the wall section of the furnace chamber;

heating the furnace chamber to a holding temperature over a first time period;

maintaining the holding temperature over a second time period;

opening the wall section of the furnace chamber for a second time to bring the seat of the wall section into a heated first cooling zone for a first cooling period;

causing a signal indicating an expiration of the first cooling period and a transition to a second cooling period corresponding to a second cooling zone to be emitted, wherein a temperature in the second cooling zone is lower than a temperature in the first cooling zone.

\* \* \* \* \*